United States Patent [19]

Guse et al.

[11] Patent Number: 4,778,678

[45] Date of Patent: Oct. 18, 1988

[54] TRANSDERMAL MEDICAMENT

[75] Inventors: Günter Guse, Hamburg; Bodo Asmussen, Ammersbek; Günter Borchert, Hamburg, all of Fed. Rep. of Germany

[73] Assignee: Beiersdorf AG, Hamburg, Fed. Rep. of Germany

[21] Appl. No.: 46,377

[22] Filed: May 4, 1987

[30] Foreign Application Priority Data

May 22, 1986 [DE] Fed. Rep. of Germany ....... 3617158

[51] Int. Cl.$^4$ .............................................. A61K 9/14
[52] U.S. Cl. .................................... 424/487; 424/484; 424/486; 424/449
[58] Field of Search ............................... 424/448, 449

[56] References Cited

U.S. PATENT DOCUMENTS

| | | | |
|---|---|---|---|
| 4,336,143 | 6/1982 | Sanvordeker | 424/449 |
| 4,661,105 | 4/1987 | Gale | 424/449 |
| 4,687,481 | 8/1987 | Nuwayser | 424/449 |

*Primary Examiner*—Thurman K. Page
*Assistant Examiner*—L. R. Horne
*Attorney, Agent, or Firm*—Sprung Horn Kramer & Woods

[57] ABSTRACT

A transdermal medicament which contains, as a suspension in a viscous matrix, at least one solid active compound or auxiliary or at least one active compound adsorbed on a solid auxiliary is characterized in that the preparation of the suspensions is carried out by wet grinding in the presence of a medium-viscosity solution of the matrix or certain constituents thereof under low heat stress and shear stress.

5 Claims, No Drawings

TRANSDERMAL MEDICAMENT

DESCRIPTION

The invention relates to a transdermal medicament, preferably in the form of a plaster, which contains, as a suspension in a viscous, preferably adhesive matrix, at least one solid active compound or auxiliary or at least one active compound adsorbed on a solid auxiliary, and to a process for preparing such a suspension.

Transdermal medicaments in the form of plasters are not actually novel, but the embodiments hitherto disclosed have various disadvantages. Transdermal medicaments of this type must in principle fulfil the functions of an active compound reservoir, release control and self-adhesion to the skin.

For reasons of simpler and more economical producibility, systems of the so-called matrix type are particularly desirable for this purpose, where a single layer ("matrix") fulfils all three of the abovementioned functions.

The production of such systems, however, causes difficulties when at least one solid active compound or auxiliary or at least one active compound adsorbed on a solid auxiliary is to be used in the form of a suspension in a matrix. Such a procedure may be necessary, for example, in order to prevent crystallization of the active compound in the matrix or in order to make the active compound easier to handle as, for example, in the case of glycerol trinitrate, or if an active compound of low solubility is concerned (for example moxonidine).

In such cases, it has not been possible with the transdermal medicaments hitherto disclosed to take equally satisfactory account of both the pharmaceutical requirements and the requirements of adhesion technology. Thus, the particle size of the pharmaceutical active compounds or auxiliaries frequently conflicts with the thickness of the matrix, with the consequence that the active compound or auxiliary particles project beyond the skin-side surface of the matrix and impair the adhesiveness of the latter, so that reliable full-area skin contact and hence the controlled active compound transport from the matrix into the skin are unavoidably impaired.

To obviate these problems, German Offenlegungsschrift No. 3,315,272 has therefore proposed a multilayer structure with a separate reservoir layer and self-adhesive layer, no (solid) carriers being added in the self-adhesive layer.

It is also observed that, when commercially available pharmaceutical active compounds or auxiliaries are used, production breakdowns occur, for example because these substances settle out after they have been mixed into the solution of the matrix polymer and thus cause an uneven distribution of the medicament. Moreover, when polymer matrices containing medicaments are coated across the surface and then dried, interfering bubbles form in particular if the particles of active compound or auxiliaries contain air occlusions which act as bubble nuclei.

It has hitherto not been possible satisfactorily to avoid these difficulties, some of which are also described, for example, in European Published Application No. 13,606, by dry comminution of the active compounds or auxiliaries before they are mixed into the matrix, either because they were not amenable to grinding, suffered changes during grinding as a result of heat and shear action, or because they formed secondary agglomerates, which were not redispersible, after the comminution had been carried out.

It was the object of the invention to develop a transdermal medicament which avoids the disadvantages described above, and to develop a process by means of which solid pharmaceutical active compounds or auxiliaries or active compounds adsorbed on solid auxiliaries can, in a single working step, be comminuted, wetted, deaerated and suspended in a matrix of adhesive, without undergoing undesirable changes due to heat or shear action.

It has been found that such a transdermal medicament can be obtained in a surprisingly simple manner when the suspension is prepared by wet grinding in the presence of a medium-viscosity solution of the matrix of adhesive (or certain constituents thereof) and is processed further in a manner known per se, provided that the grinding step proceeds under low heats and shear stress in a mill with freely mobile grinding bodies. In particular, the conventional ball mill, that is to say a horizontal, slowly rotating cylinder with a freely mobile bed of balls, has proved to be an outstandingly suitable instrument. In order to minimize abrasion and contamination of the product, grinding drums and balls of hard porcelain are preferred for pharmaceutical purposes. The speed of rotation is adjusted such that there is very pronounced frictional rolling motion of the balls (cascading); $n = 10/\sqrt{Di}$ ($n$=speed of rotation in min.$^{-1}$; $Di$=internal diameter of the drum in m) can be taken as a guide value. The power input to the mill is then so low that the material being ground is warmed only insignificantly (from room temperature to about 30° C.).

In the preparation of active substance suspensions for transdermal medicaments, it is frequently necessary to distribute the pharmaceutical active compound or auxiliary evenly in a highly viscous polymer system. It can then be preferable not to introduce the entire polymer phase into the ball mill but only certain portions thereof, so that the fluid phase predominantly has a moderate viscosity (preferably 100 to 300, especially 200 mPa s) during the grinding process. If the wet grinding were carried out exclusively in the presence of a low-viscosity fluid, i.e. for example an organic solvent, an undesirably high abrasion of drum and balls would result.

For the preferred embodiment of producing a nitrate-containing plaster with glycerol trinitrate as the active compound, which is mentioned here as a not in any way restrictive example, an advantageous and particularly preferred division of the polymer components is given in Example 1.

In the process described in that example, it is possible to reduce the mean particle size of the lactose used (from initially 80 μm) in the ball mill to 20 μm within 16 hours. At the same time, the tendency of the finished preparation to settle out is greatly reduced and the formation of hard sediments which are no longer redispersible, as is possible in processes of the state of the art, is completely excluded.

Both the grinding action and the prevention of sedimentation can be further favoured if required, in an embodiment of the invention, by adding small quantities of surface-active substances to the ball mill charge. These can be, for example, fatty alcohol ethoxylates, sorbitan ester ethoxylates and sulphated castor oils in quantities of about 0.2 to 1% by weight of the charge.

If a particularly fast process for forming the suspension is desired, it is also possible, according to another embodiment of the invention, in the case of systems which are less sensitive to heat and shear, to use mills with a higher power input, such as, for example, a stirred ball mill (bead mill), where a pre-suspension is pumped through an upright cylinder in which a high-speed stirrer element sets a bed balls into circulation.

However, in the preparation, as described, of a suspension as part component of a coating composition for a nitrate-containing plaster, the preparation of a pre-suspension is unnecessary. This process according to the preferred embodiment of the invention also has, at the same time, an important advantage. The preferably used, commercially available triturate of 10% of glycerol trinitrate and 90% of lactose is included, according to the regulations applicable in the Federal Republic of Germany, in Hazard Class B of Accident Prevention Regulation 41 of the Liability Association of the Chemical Industry (UVV 41) and is thus subject to more stringent safety requirements. By contrast, the finished suspension from the ball mill is one of the substances of Hazard Group C, which can be handled more easily, even after it has been completely freed from solvents. Thus, in the ball mill which can readily be inertized and firmly sealed, a glycerol trinitrate preparation which is safe to handle is produced under mild conditions which are particularly favourable both for product safety and working safety. If required, safe handling can be yet further improved by partially replacing the solvent (normally n-heptane) by toluene, acetone or ethyl acetate.

Coating compositions for transdermal medicaments of the matrix type, which have been prepared using the suspensions according to the invention, can be applied in a manner known per se to two-dimensional carrier materials and dried thereon. On drying, they show a considerably reduced tendency to form bubbles, as compared with coating compositions of the state of the art.

The adhesive properties of plasters produced according to the invention, that is to say the subjectively felt tackiness to the touch (immediate adhesion, tack) and the bonding strength to the skin during the usual wearing period of 24 hours or more, are markedly better than those according to the state of the art. Thus, the transdermal medicaments according to the present invention meet an essential condition for uniform controlled transport of active compound from the plaster matrix into the skin.

The invention is explained in more detail by the examples which follow, without being restricted to the embodiments mentioned therein. The abbreviation PBW means parts by weight.

EXAMPLE 1

The following substances are filled one after the other into a hard porcelain ball mill:
39.86 PBW of a 60% solution of polyisobutene of $M_v=40,000$ in n-heptane
91.95 PBW of n-heptane
6.43 PBW of a 5% solution of glycerol trinitrate in neutral oil
1.03 PBW of sulphated castor oil and
37.57 PBW of an aliphatic hydrocarbon resin having an R+K softening point of 97° C.

The mill is sealed and then rotated for 1 hour in order to homogenize the contents. The following is then filled in:

85.36 PBW of a 10% triturate of glycerol trinitrate on lactose.

The resealed mill is then rotated for about 20 hors. After this time, a homogeneous yellowish suspension having a viscosity of about 250 mPa s has formed. A grindometer measurement shows that the particle size of the lactose has been reduced from initially 80 μm to a maximum of 25 μm.

The suspension is mixed by stirring with a homogeneous viscose solution, produced in a kneader, of
41.37 PBW of polyisobutene of $\overline{M}_v=2,800,000$
33.95 PBW of a 60% solution of polyisobutene of $\overline{M}_v=40,000$ in n-heptane and
177.55 PBW of n-heptane.

This mixture is a self-adhesive composition which is ready for coating and can be used in a manner known per se for the preparation of a self-adhesive plaster with glycerol trinitrate.

EXAMPLE 2

A copolymer of
65% by weight of 2-ethylhexyl acrylate
15% by weight of n-butyl acrylate and
20% by weight of N-vinylpyrrolidone
is prepared by solution polymerization in petroleum spirit/acetone (K value 74.3).

249.4 g of this polymer solution, the solids content of which is 39.7%, are ground with 1.0 g of moxonidine for 24 hours in a hard porcelain ball mill.

The result is a homogeneous active compound suspension, which is largely free of sediment and is ready for coating.

We claim:

1. Process for preparing a suspension of active compound for a transdermal medicament, characterized by wet grinding of at least one solid active compound selected from the group consisting of Glycerol trinitrate and monoximide or of at least one of said active compounds adsorbed on a solid in the presence of a solution of the matrix polymer or certain constituents thereof of a viscosity of about 100 to 300 mPa, the grinding process being carried out under low shear stress and heat stress in a mill with freely mobile grinding bodies.

2. Transdermal medicament according to claim 1, characterized in that the active compound is glycerol trinitrate and the solid is lactose.

3. Transdermal medicament according to claim 1, characterized in that the solid active compound is moxonidine.

4. Process according to claim 1, characterized in that it is carried out in a ball mill.

5. Process according to claim 1, characterized in that small quantities of surface-active substances are added for grinding.

* * * * *